United States Patent [19]

Carissimi et al.

[11] 4,085,223

[45] Apr. 18, 1978

[54] HALOGENATED DERIVATIVES OF 1,3-DIOXOLANE HAVING MUCOLYTIC ACTIVITY

[75] Inventors: Massimo Carissimi; Franco Ravenna; Giorgio Cantarelli, all of Milan, Italy

[73] Assignee: Maggioni & C. S.p.A., Milan, Italy

[21] Appl. No.: 670,174

[22] Filed: Mar. 24, 1976

[30] Foreign Application Priority Data

Apr. 2, 1975 Italy .................................. 21929 A/75

[51] Int. Cl.$^2$ .................... A61K 31/335; C07D 317/10
[52] U.S. Cl. ............................... 424/278; 260/340.9 R
[58] Field of Search .................. 260/340.9 R; 424/278

[56] References Cited

U.S. PATENT DOCUMENTS

| 2,589,296 | 3/1952 | Schroeder | 260/340.9 X |
| 2,872,378 | 2/1959 | Manchey et al. | 260/340.9 X |
| 3,812,261 | 5/1974 | Hartmann | 260/340.9 X |
| 3,996,376 | 12/1976 | Hartmann | 424/278 |

OTHER PUBLICATIONS

Theilheimer, Synthetic Methods of Organic Chemistry, vol. 16, abstract 612.

*Primary Examiner*—Ethel G. Love
*Attorney, Agent, or Firm*—Michael J. Striker

[57] ABSTRACT

Compounds useful as expectorants and fluidizers of tracheobronchial mucus having the specified formula are disclosed, the compounds having at least one bromine or iodine atom as a substituent. A process for preparing such compounds is also disclosed.

10 Claims, No Drawings

HALOGENATED DERIVATIVES OF 1,3-DIOXOLANE HAVING MUCOLYTIC ACTIVITY

This invention relates to some 4-hydroxymethyl-2-(bromoalkyl)-1,3-dioxolanes and 4-hydroxymethyl-2-(iodoalkyl)-1,3-dioxolanes useful as expectorants and fluidizers of tracheobronchial mucus. As an expectorant and fluidizer, the action of iodine in the form of mineral salts, particularly alkaline mineral salts, has been described in many scientific articles (for example, refer to E. M. BOYD in Pharmacological Reviews Vol. 6, page 521; (1954) ). However, in such reports it is pointed out that organic derivatives of iodine are completely lacking in such pharmacological properties and the use thereof in medicine was up to that time restricted to contrast agents in radiological investigations.

Conversely, the compounds according to the present invention are organic derivatives of iodine, in which the characteristic pharmacological properties for said element as ion are retained, the brominated analogs unexpectedly also exhibiting the above mentioned features. The general formula of the compounds is as follows:

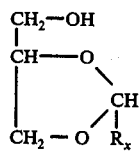

wherein $R_x$ is a linear or branched alkyl radical having 1 to 4 carbon atoms and in which at least one atom of iodine or bromine is present as a substituent.

These compounds have shown a capability of increasing up to 150% the secretion of laryngobronchial fluid in tracheotomized rabbits, while reducing the viscosity of said fluid. Furthermore, when administered to a human being in daily doses ranging from 30 to 500 mg, such compounds have aided in freeing airways obstructed or blocked by catarrh and mucus, since due to reduced viscosity the mucus was removable without any difficulty.

The method for preparing the compounds consists of condensing an acetal having the following general formula:

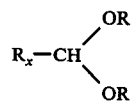

wherein $R_x$ is the same as above specified and R is an alkyl radical having 1 to 3 carbon atoms, with 1-benzylglycerol, thereby respectively obtaining 4-benzyloxy-2-(iodoalkyl)-1,3-dioxolanes and 4-benzyloxy-2(bromoalkyl)-1,3-dioxolanes having the following general formula:

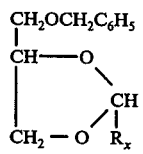

The benzyl group is removed from these dioxolanes by catalytic hydrogenation, providing the compounds according to the invention.

A variant to this method, restricted to iodo-derivatives only, consists of reflux heating the bromo-derivatives in a suitable solvent for bromo-derivatives in the presence of an alkali metal iodide, thus resulting in iodine substituting for bromine.

The substances so obtained are pure at elemental analyses and consist in a mixture, in nearly constant proportions for each of the derivatives, of the two geometrical isomers as provided by theory and due to the relative positions of radical $R_x$ and hydroxymethyl group in the dioxolane ring.

EXAMPLE 1

Cis, trans-4-benzyloxymethyl-2-bromo-methyl-1,3-dioxolane 182 gr 1-benzylglycerol, 226 gr bromoacetaldeydiethylacetal and 18 gr sulphosalicylic acid were heated for 2 hours at 100° C under stirring. After cooling, the reaction mixture was diluted with ether, and the ether solution washed with a saturated aqueous solution of sodium bicarbonate and dried. An oil was obtained by ether evaporation and distilled. B.p. 150° C/0.5 mmHg.

EXAMPLE 2

Cis, trans-4-benzyloxymethyl-2-(1-bromoethyl)-1,3 dioxolane.

182 gr 1-benzylglycerol, 242 gr α-bromopropionaldheydediethylacetal and 18 gr sulphosalicylic acid were heated for 2 hours at 100° C under stirring. After cooling, the reaction mixture was diluted with ether, and the ether solution washed with a saturated aqueous solution of sodium bicarbonate and dried. An oil was obtained by ether evaporation and distilled. B.p. 195° C/0.5 mmHg.

EXAMPLE 3

Cis-trans-4-benzyloxymethyl-2-iodomethyl-1,3-dioxolane.

182 gr 1-benzylglycerol, 280 gr iodoacetaldheydediethylacetal and 18 gr sulphosalicylic acid were heated for 2 hours at 100° C under stirring. After cooling, the reaction mixture was diluted with ether, and the ether solution washed with a saturated aqueous solution of sodium bicarbonate and dried. An oil was obtained by ether evaporation and distilled. B.p. 170° C/0.5 mmHg.

EXAMPLE 4

Cis- trans-4-oxymethyl-2-bromoethyl-1,3-dioxolane.

287 gr cis, trans-4-benzyloxymethyl-2-bromoethyl-1,3-dioxolane were dissolved in 5000 ml methanol and stirred in hydrogen atmosphere in the presence of 60 gr 5% Pd on carbon. When one hydrogen molecule was taken up, the catalyst was filtered off, the solvent removed and the residual oil distilled. B.p. 102° C/0.8 mmHg.

The mixture comprised 69% cis isomer and 31% trans isomer (gas liquid chromatography).

EXAMPLE 5

Cis, trans-4-oxymethyl-2-(1-bromoethyl)-1,3 dioxolane.

301 gr cis, trans-4-benzyloxymethyl-2-(1-bromoethyl)-1,3-dioxolane were dissolved in 5000 ml methanol and stirred in hydrogen atmosphere in the presence of 60 gr 5% Pd on carbon. When one hydrogen molecule was taken up, the catalyst was filtered off, the solvent removed and the residual oil distilled. B.p. 100° C/0.8 mmHg.

The mixture comprised 60% cis isomer and 40% trans isomer. (Gas liquid chromatography).

EXAMPLE 6

Cis, trans-4-oxymethyl-2-iodomethyl-1,3-dioxolane (from cis, trans-4-benzyloxymethyl-2-iodomethyl-1,3-dioxolane).

334 gr cis, trans-4-benzyloxymethyl-2-iodomethyl-1,3-dioxolane were dissolved in 5000 ml methanol and stirred in hydrogen atmosphere in the presence of 60 gr 5% Pd on carbon. When one hydrogen molecule was taken up, the catalyst was filtered off, the solvent evaporated and the residual oil kept at 30° C for 2.5 hours under 0.5 mmHg. Following this treatment, the product was pure at elemental analysis. It could not be distilled as it would decompose.

The mixture comprised 71% cis isomer and 29% trans isomer. (Gas liquid chromatography).

EXAMPLE 7

Cis, trans-4-oxymethyl-2-iodomethyl-1,3-dioxolane (from cis, trans-4-oxymethy-2-bromomethyl-1,3-dioxolane).

20 gr cis, trans-4-oxymethy-2-bromomethyl-1,3-dioxolane and 20 gr sodium iodide, dissolved in 200 ml anhydrous acetone, were heated for 2' hours at 130° C in an autoclave. After cooling, the solvent was evaporated under reduced pressure and the residue taken up with 200 ml water and extracted with ethyl acetate. This solution was then washed with a solution of 1% sodium hyposulphite and water, then dried and the solvent was removed. The residual oil was kept at 30° C for at least 2 hours under 0.5 mmHg. Following this treatment, the product was pure at elemental analysis. It could not be distilled as it would decompose.

The mixture comprised 69% cis isomer and 31% trans isomer. (Gas liquid chromatography).

What we claim is:

1. A substance comprising a mixture of the cis- and trans-isomers of 4-hydroxymethyl-2-monohaloalkyl-1,3-dioxolane having the formulae

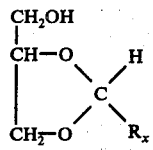 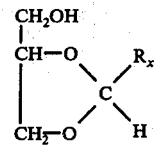

cis                     trans wherein $R_x$ is selected from monobromoalkyl, alkyl having 1–4 carbon atoms and iodomethyl.

2. A substance according to claim 1 designated cis-trans-4-hydroxymethyl-2-bromoethyl-1,3-dioxolane.
3. A substance according to claim 1 designated cis-trans-4-hydroxymethyl-2-iodomethyl-1,3-dioxolane.
4. A substance according to claim 1 designated cis-trans-4-hydroxymethyl-2-(1-bromoethyl)-1,3-dioxolane.
5. A therapeutic composition useful as an expectorant and fluidizer of tracheobronchial mucus comprising an expectorant or fluidizing effective amount of the compound of claim 1.
6. A method for increasing the secretion of laryngobronchial fluid while reducing the viscosity of such fluid comprising administering to a mammal having such condition an expectorant or fluidizing effective amount of a substance according to claim 1.
7. A method according to claim 6 which comprises administering said substance in an amount of from 30 to 500 mg per day.
8. A process for preparing the compounds of claim 1 in which halo designates iodo comprising heating a compound of the formula

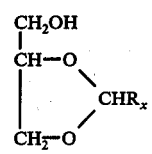

in which $R_x$ is monobromoalkyl, alkyl having 1 to 4 carbon atoms in the presence of a solvent and of an alkali metal iodide.

9. The process of claim 8 wherein the heating is carried out under pressure in an autoclave.
10. The process of claim 8 wherein the solvent is an aliphatic ketone.

* * * * *